(12) United States Patent
Kraemer et al.

(10) Patent No.: US 10,806,410 B2
(45) Date of Patent: Oct. 20, 2020

(54) METHOD, ARRANGEMENT, COMPUTER PROGRAM PRODUCT AND COMPUTER-READABLE MEDIUM FOR AUTOMATICALLY DETERMINING PATIENT WEIGHT WITH A PATIENT POSITIONING DEVICE

(71) Applicant: SIEMENS HEALTHCARE GMBH, Erlangen (DE)

(72) Inventors: Alexander Kraemer, Irchenrieth (DE); Matthias Mueller, Bamberg (DE); Josef Zeidler, Marktredwitz (DE)

(73) Assignee: Siemens Healthcare GmbH, Erlangen (DE)

( * ) Notice: Subject to any disclaimer, the term of this patent is extended or adjusted under 35 U.S.C. 154(b) by 333 days.

(21) Appl. No.: 15/828,693

(22) Filed: Dec. 1, 2017

(65) Prior Publication Data

US 2018/0153484 A1 Jun. 7, 2018

(30) Foreign Application Priority Data

Dec. 1, 2016 (DE) .................. 10 2016 223 930

(51) Int. Cl.
| | | |
|---|---|---|
| *G06F 11/30* | (2006.01) | |
| *A61B 6/04* | (2006.01) | |
| *G01G 3/16* | (2006.01) | |
| *G01G 19/44* | (2006.01) | |
| *G01G 19/52* | (2006.01) | |
| *A61B 6/03* | (2006.01) | |

(52) U.S. Cl.
CPC .......... *A61B 6/0457* (2013.01); *A61B 6/0471* (2013.01); *G01G 3/16* (2013.01); *G01G 19/445* (2013.01); *G01G 19/52* (2013.01); *A61B 6/032* (2013.01)

(58) Field of Classification Search
CPC .................................... A61B 6/0457
See application file for complete search history.

(56) References Cited

U.S. PATENT DOCUMENTS

| | | | |
|---|---|---|---|
| 3,354,698 A | 11/1967 | Christmann | |
| 4,856,604 A | 8/1989 | Sisson et al. | |
| 2008/0249378 A1 | 10/2008 | Brauers et al. | |
| 2009/0252300 A1 | 10/2009 | Schwartz et al. | |
| 2011/0226035 A1* | 9/2011 | Date | G01G 19/50 73/1.13 |
| 2013/0008726 A1* | 1/2013 | Eberler | A61B 5/0555 177/1 |

FOREIGN PATENT DOCUMENTS

| | | |
|---|---|---|
| CN | 101282686 A | 10/2008 |
| CN | 101548888 A | 10/2009 |

(Continued)

*Primary Examiner* — Phuong Huynh
(74) *Attorney, Agent, or Firm* — Laurence Greenberg; Werner Stemer; Ralph Locher

(57) ABSTRACT

A method automatically determines a weight of a patient lying on a tabletop of a patient positioning device. A motorized movement of the tabletop along at least one predeterminable axis sets the tabletop in an oscillation via an elastic drive train element, and the patient's weight is determined from a determined oscillation frequency. Therefore, the weight of a patient lying on a patient positioning device can be determined in a simple manner.

14 Claims, 3 Drawing Sheets

(56) References Cited

FOREIGN PATENT DOCUMENTS

| | | |
|---|---|---|
| CN | 102078199 A | 6/2011 |
| CN | 102265123 A | 11/2011 |
| DE | 3910731 A1 | 10/1989 |
| DE | 102011078567 A1 | 1/2013 |
| DE | 102012201783 A1 | 8/2013 |
| DE | 102013223537 A1 | 3/2015 |

* cited by examiner

METHOD, ARRANGEMENT, COMPUTER PROGRAM PRODUCT AND COMPUTER-READABLE MEDIUM FOR AUTOMATICALLY DETERMINING PATIENT WEIGHT WITH A PATIENT POSITIONING DEVICE

CROSS-REFERENCE TO RELATED APPLICATION

This application claims the benefit, under 35 U.S.C. § 119, of German patent application DE 10 2016 223 930.9, filed Dec. 1, 2016; the prior application is herewith incorporated by reference in its entirety.

BACKGROUND OF THE INVENTION

Field of the Invention

The invention relates to a method, an arrangement, a computer program product and a computer-readable medium for automatically determining a patient's weight of a patient lying on the tabletop of a patient positioning device. For this purpose the oscillation of the tabletop during movement is analyzed.

For the administration of medications or contrast agents in medical imaging, frequently the weight of the patient must be known. Patients who are able to stand can be weighed with the aid of personal scales. The physician can only estimate the weight of patients who are unable to stand or are even unconscious. If the patient is lifted by motorized measures, for example using a lift drive in a patient couch, the power consumption of the lift drive can also be used to estimate the approximate weight of the patient.

Published, non-prosecuted German patent application DE 10 2012 201 783 A1 specifies a further method for determining the weight of a patient on a patient positioning device. The patient positioning device has a table-foot and a tabletop guided displaceably thereupon for positioning the patient. At least one force sensor is mounted on the table-foot for the purpose of determining the weight.

Published, non-prosecuted German patent application DE 10 2013 223 537 A1 shows a patient positioning device in which a tabletop, also referred to as a reclining board, can be displaced horizontally by a toothed belt and a motorized drive unit.

SUMMARY OF THE INVENTION

It is an object of the invention to specify a method, an arrangement, a computer program product and a computer-readable medium for determining a patient's weight with a patient positioning device, which enable a precise determination of the patient's weight of a patient lying down and represent an alternative to the prior art.

In accordance with the invention, the stated object is achieved with the method, the arrangement, the computer program product, and the computer-readable medium for determining the patient's weight with a patient positioning device as claimed in the independent claims. Advantageous developments are disclosed in the dependent claims.

In accordance with the invention an elastic component (e.g. a toothed belt) is located in the drive train of an axis of the patient positioning device (e.g. for the purpose of moving the patient longitudinally), which produces an oscillating mass-spring system, wherein the patient mass represents part of the oscillating mass and the elasticity of the toothed belt represents the spring stiffness. The frequency of the mass-spring system is indirectly proportional to the oscillating mass. For a clean movement, the drive controller has to compensate for the system's tendency to oscillate, and so the oscillation becomes visible in the drive controller's control output, especially in the motor current. Dynamically recording the motor current and determining the oscillation frequency of the motor current allows the patient weight to be determined.

Analyzing the motor's control variables (in particular the motor current) in respect of amplitude and frequency allows physical characteristics to be determined that correlate directly with the patient weight. Explicitly weighing the patient using personal scales—if this is even possible—can be omitted, and the direct correlation can result in better accuracy than with known methods.

The invention claims a method for automatically determining a patient's weight of a patient lying on the tabletop of a patient positioning device. A motorized movement of the tabletop along at least one predeterminable axis sets the tabletop in an oscillation by an elastic drive train element, and the patient's weight is determined from the determined oscillation frequency. Patient, tabletop and drive train form a mass-spring system that is capable of oscillation, the frequency of which is indirectly proportional to the patient's mass.

The invention offers the advantage that the weight of a patient lying on a patient positioning device can be determined in a simple manner.

In one development, the patient's weight can be determined by comparison with frequency values determined empirically in advance. For this purpose, weights simulating the weight of the patient are placed on the tabletop, for example.

In a further embodiment, the oscillation of the tabletop can be reduced by a motor controller, wherein the patient's weight can be determined from the oscillation frequency of at least one control parameter of the motor controller. The motor controller is configured such that an oscillation of the tabletop is compensated for, wherein the control parameter exhibits the same frequency.

In a further embodiment, the control parameter is the motor current, the oscillation frequency of which can be determined in a simple manner.

In a further variant, a mean patient weight value can be formed on the basis of the movement of the tabletop along multiple axes. The determination of the patient's weight becomes more accurate as a result.

In one development, in a predeterminable time interval the motor controller can be performed with a high tendency to oscillate. For this purpose the control parameters of the motor controller are configured accordingly.

Furthermore, before the patient's weight is determined, the tabletop can be moved without a patient, wherein the variance in the determined frequency from a determined initial frequency value is used for compensation and/or calibration purposes. It is possible to compensate for example for the influences of wear and tear on the drive train as a result.

The invention also claims an arrangement for automatically determining the patient weight, having:
a) a patient positioning device,
b) a tabletop of the patient positioning device for positioning a patient, which can be displaced along at least one axis,
c) an elastic drive train element, which is configured to displace the tabletop along the axis, d) a motorized drive unit that acts on the drive train element, which is configured, by means of the drive train element, to set the tabletop in an oscillation along the axis, and
e) an oscillation measurement unit, which is configured to determine the oscillation frequency of the tabletop, and from this the patient's weight.

In one development of the arrangement, the drive train element can have a toothed belt that has an elastic effect.

In a further embodiment, the oscillation measurement unit can be configured to determine the patient weight by comparison with frequency values determined empirically in advance.

In one development, the arrangement has:
a) a motor control unit of the motorized drive unit, which is designed to reduce the oscillation of the tabletop, and
b) wherein the oscillation measurement unit is configured to determine the patient weight from the oscillation frequency of at least one control parameter of the motor control unit.

In a further embodiment, the control parameter can be the motor current of the motorized drive unit.

Furthermore, the invention claims a computer program product having a computer program. The computer program can be loaded into a storage device of an oscillation measurement unit and the steps of a method in accordance with the invention are carried out with the computer program when the computer program is executed in the oscillation measurement unit.

Finally, the invention claims a computer-readable medium on which a computer program is stored. The computer program can be loaded into a storage device of an oscillation measurement unit and the steps of a method in accordance with the invention can be carried out with the computer program when the computer program is executed on the oscillation measurement unit.

Other features which are considered as characteristic for the invention are set forth in the appended claims.

Although the invention is illustrated and described herein as embodied in a method, an arrangement, a computer program product and a computer-readable medium for automatically determining a patient's weight with a patient positioning device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF AN EXEMPLARY EMBODIMENT

Figure 1:
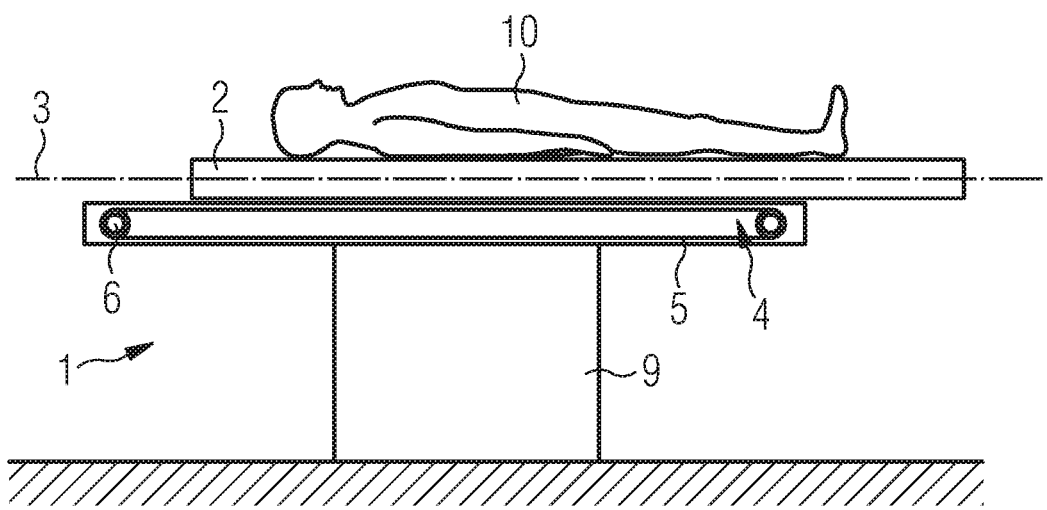
FIG. 1 is an illustration showing a patient positioning device.

Referring now to the figures of the drawings in detail and first, particularly to FIG. 1 thereof, there is shown side view of a patient positioning device 1. The patient positioning device 1 has a tabletop 2 which can be displaced horizontally along the axis 3, the tabletop being mounted on a height-adjustable table-foot 9. A patient 10, whose patient's weight is to be determined, is located on the tabletop 2.

The tabletop 2 can be moved along the axis 3 by a motorized drive unit 6, for example by an AC motor acting on a toothed belt 5 of a drive train unit 4. The toothed belt 5 has a slightly elastic effect, as a result of which the tabletop 2 is undesirably set in an oscillation that is compensated for by a motor control.

Figure 2:
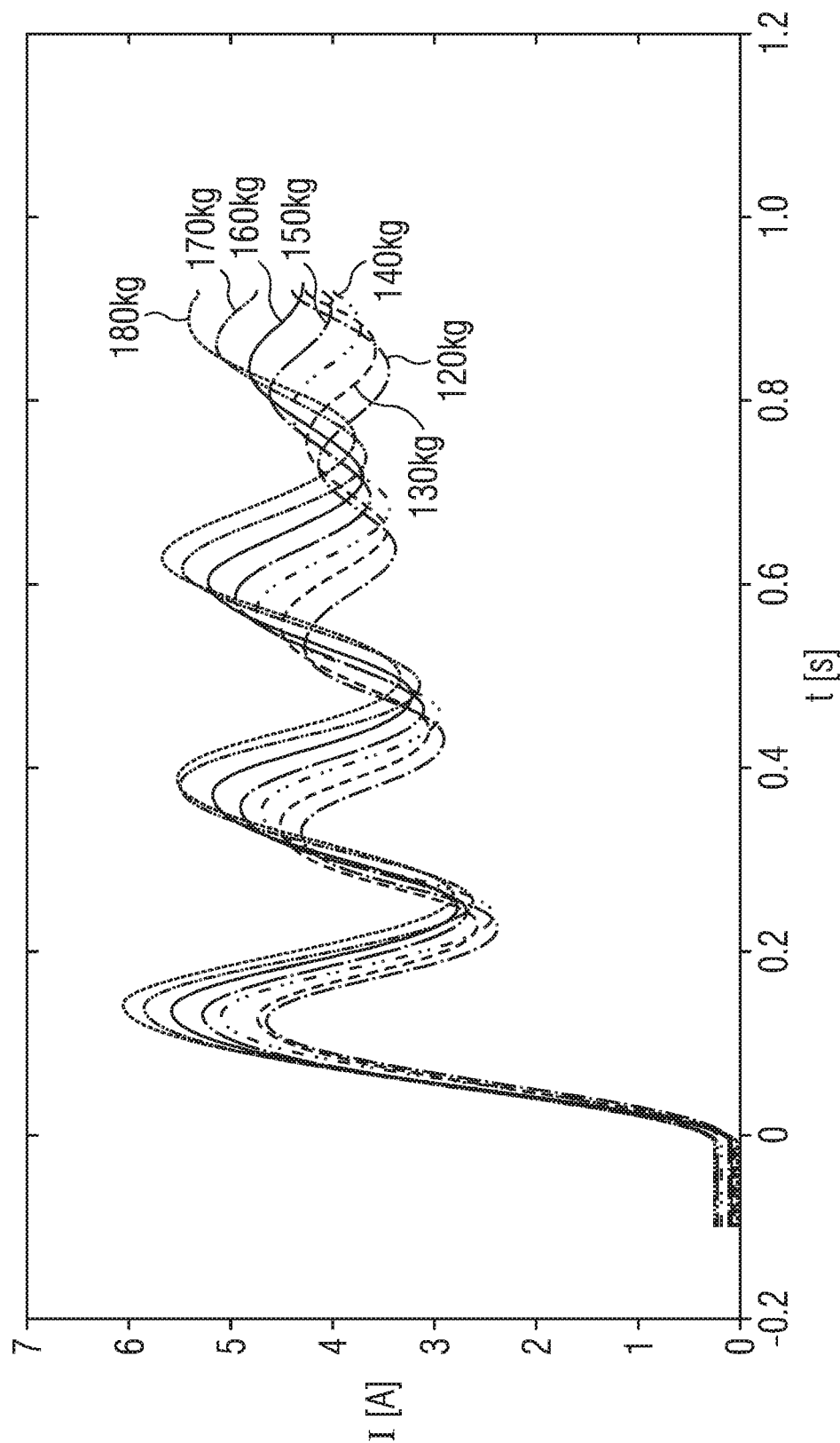
FIG. 2 is a graph plotting a motor current over patient weight and time.

In FIG. 2 a graph is shown plotting the motor current I of the motor control in amperes over time t in seconds for different patient weights from 120 kg to 180 kg. The inversely proportional relationship between the frequency of the motor current I and patient weight can be seen clearly. If the frequencies for different patient weights are determined empirically in advance and stored, determining the frequency of the motor current I allows the current patient weight to be determined in a simple manner by comparison with and interpolation of the stored values. The graph in FIG. 3 shows an example of how this can be done in an operational setting.

Figure 3:
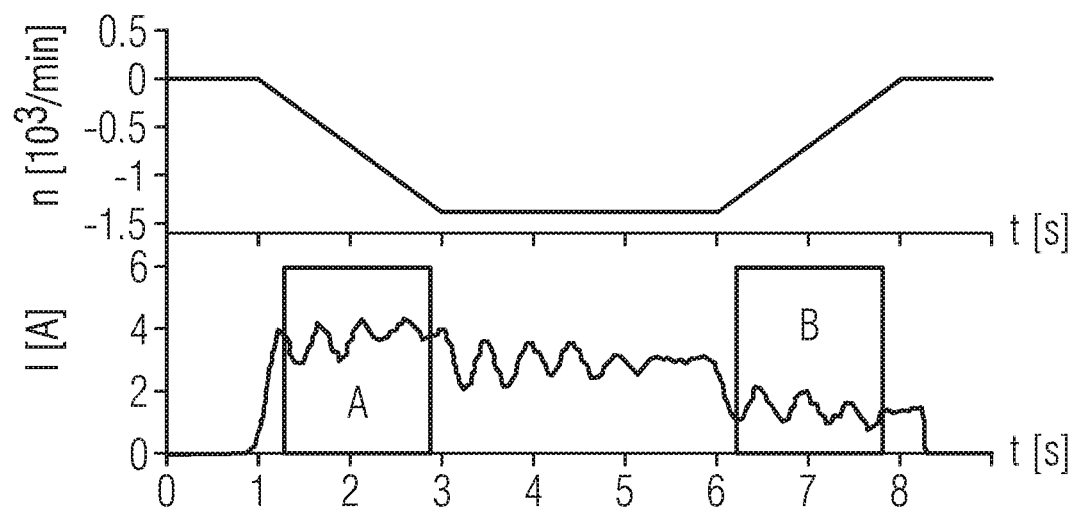
FIG. 3 is a graph plotting the motor current over time and movement phases (acceleration, constant velocity)

FIG. 3 shows a graph of the rotational speed n in revolutions per minute and the motor current I in amperes of a motorized drive unit 6 plotted over time t in seconds. A motor control compensates for oscillations in the motor current I. The oscillation of the tabletop 2 is excited each time the acceleration is changed, i.e. at the start (region A) and end (region B) of the movement of the tabletop 2, and at the transition to the movement phase with constant velocity (i.e. between regions A and B). Using the method described, the frequency and therefore the patient weight can be determined from each phase. Averaging the three individual weights determined allows the overall accuracy to be increased.

Figure 4:
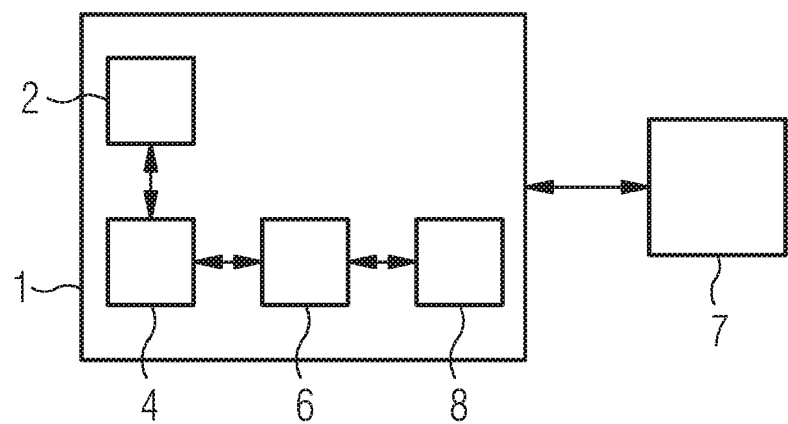
FIG. 4 is a block diagram for determining a patient's weight with the aid of the patient positioning device.

FIG. 4 shows a block diagram of an arrangement for determining the patient weight with the aid of a patient positioning device 1. By means of the elastic drive train element 4, the tabletop 2 is set in motion by the motorized drive unit 6. The motor control unit 8 compensates for the oscillation of the tabletop 2 by regulating the motor current I. The frequency of the motor current I is a measure of the oscillation of the tabletop 2 and can be determined by oscillation measurement unit 7. The current patient weight can be inferred by comparison with frequencies determined in advance with different patient weights. The oscillation measurement unit 7 can also be designed as a control unit that controls the entire weight determination process.

If multiple axes of the tabletop 2 are motorized (e.g. for a CT table typically having up to 3 axes), the method can be applied to each axis so that the patient's weight can be determined multiple times. Averaging these values then allows the overall accuracy to be increased further.

The configuration of the control parameters of the motor control unit 8 is normally selected so that the tendency of the tabletop 2 to oscillate is reduced. When determining weight in accordance with this method, an oscillation is desirable in order to be able to work with different parameter sets: a first parameter set for a "weight measurement run" with a high tendency to oscillate, and another second parameter set for normal operation with minimized oscillation.

Variations in the drive train element 4 (e.g. in the tension of the toothed belt; caused by abrasive influences in the patient positioning device 1; or caused by thermal influences) mean that the accuracy of the method described is limited. Determining and then compensating for the influences of these variations is possible by a dry run without a patient 10 (="calibration run").

Although the invention has been illustrated and described in detail based on the preferred exemplary embodiments, the invention is not restricted by the examples given and other variations can be derived therefrom by a person skilled in the art without departing from the protective scope of the invention.

The following is a summary list of reference numerals and the corresponding structure used in the above description of the invention:
1 Patient positioning device
2 Tabletop
3 Axis
4 Drive train element
5 Toothed belt
6 Motorized drive unit
7 Oscillation measurement unit
8 Motor control unit
9 Table-foot
10 Patient
A, B Region
I Motor current
n Motor rotational speed
t Time

The invention claimed is:

1. A method for automatically determining a weight of a patient lying on a tabletop of a patient positioning device, which comprises the steps of:
   inducing a motorized movement of the tabletop along at least one predeterminable axis, including a horizontal axis, for setting the tabletop in oscillation by means of an elastic drive train and horizontally displacing the tabletop in at least a horizontal direction by the elastic drive train; and
   determining the weight of the patient from a determined oscillation frequency of the tabletop.

2. The method according to claim 1, which further comprises determining the weight of the patient by a comparison with frequency values determined empirically in advance.

3. The method according to claim 1, which further comprises reducing the oscillation of the tabletop via a motor controller, the weight of the patient can be determined from the determined oscillation frequency of at least one control parameter of the motor controller.

4. The method according to claim 3, wherein the control parameter is a motor current.

5. The method according to claim 1, which further comprises forming a mean patient weight value on a basis of the motorized movement of the tabletop along multiple axes.

6. The method according to claim 3, wherein in a predeterminable time interval the motor controller can create a tendency for oscillation.

7. The method according to claim 1, wherein:
   before the weight of the patient is determined, moving the tabletop without the patient; and
   a variance in a determined frequency from a determined initial value is used for compensation and/or calibration purposes.

8. A configuration for automatically determining a weight of a patient, the configuration comprising:
   a patient positioning device having a tabletop for positioning the patient, said tabletop being displaceable along at least one axis, including a horizontal axis;
   an elastic drive train configured to displace said tabletop along said axis;
   a motorized drive unit acting on said elastic drive train, said motorized drive unit is configured, by means of said elastic drive train, to set said tabletop in oscillation along the axis and horizontally displacing said tabletop in at least a horizontal direction by said elastic drive train; and
   an oscillation measurement unit configured to determine an oscillation frequency of the tabletop, and from the oscillation frequency the weight of the patient is determined.

9. The configuration according to claim 8, wherein said elastic drive train has a toothed belt.

10. The configuration according to claim 8, wherein said oscillation measurement unit is configured to determine the weight of the patient by a comparison with frequency values determined empirically in advance.

11. The configuration according to claim 8,
    further comprising a motor control unit for said motorized drive unit and configured to reduce the oscillation of said tabletop; and
    wherein said oscillation measurement unit is configured to determine the weight of the patient from an oscillation frequency of at least one control parameter of said motor control unit.

12. The configuration according to claim 11, wherein the control parameter is a motor current of said motorized drive unit.

13. A computer program product comprising computer executable instructions which can be loaded into a storage device of an oscillation measurement unit, said computer executable instructions carrying out the method according to claim 1 when the computer executable instructions are executed in the oscillation measurement unit.

14. A non-transitory computer-readable medium having computer executable instruction which are to be loaded into a storage device of an oscillation measurement unit, said computer executable instructions carrying out the method according to claim 1 when the computer executable instructions are executed in the oscillation measurement unit.

* * * * *